United States Patent [19]

Kurth et al.

[11] Patent Number: 4,590,930
[45] Date of Patent: May 27, 1986

[54] FIXATION DEVICE AND PROCESS FOR AN INTRAMEDULLARY NAIL

[75] Inventors: Lloyd A. Kurth, 255 Randolph Rd., Morgantown, W. Va. 26505; J. David Blaha, Morgantown, W. Va.

[73] Assignee: Lloyd A. Kurth, Morgantown, W. Va.

[21] Appl. No.: 506,779

[22] Filed: Jun. 22, 1983

[51] Int. Cl.⁴ ............................................. A61F 5/04
[52] U.S. Cl. .............................. 128/92 BC; 128/92 B
[58] Field of Search ............ 128/92 B, 92 BA, 92 BB, 128/92 BC, 92 CA

[56] References Cited

U.S. PATENT DOCUMENTS

| | | |
|---|---|---|
| 2,821,979 | 2/1958 | Cameron .................... 128/92 BC |
| 3,216,414 | 11/1965 | Street . |
| 3,678,925 | 7/1972 | Fischer et al. . |
| 3,716,051 | 2/1973 | Fischer . |
| 3,759,257 | 9/1973 | Fischer et al. . |
| 3,760,802 | 9/1973 | Fischer et al. . |
| 3,779,239 | 12/1973 | Fischer et al. . |
| 3,782,374 | 1/1974 | Fischer . |
| 3,986,504 | 10/1976 | Avila . |
| 4,091,806 | 5/1973 | Aginsky . |
| 4,204,531 | 5/1980 | Aginsky . |
| 4,227,518 | 10/1980 | Aginsky . |
| 4,236,512 | 12/1980 | Aginsky . |
| 4,237,875 | 12/1980 | Termanini . |
| 4,262,665 | 4/1981 | Rolstad et al. . |
| 4,275,717 | 6/1981 | Belesky . |
| 4,453,539 | 6/1984 | Raftopoulos et al. ......... 128/92 BC |

FOREIGN PATENT DOCUMENTS

| | | |
|---|---|---|
| 765757 | 5/1953 | Fed. Rep. of Germany ... 128/92 BC |
| 2542263 | 3/1977 | Fed. Rep. of Germany . |
| 1158993 | 6/1958 | France ......................... 128/92 BC |

Primary Examiner—Gene Mancene
Assistant Examiner—C. W. Shedd
Attorney, Agent, or Firm—Sixbey, Friedman & Leedom

[57] ABSTRACT

Both a bone fixation device and a method for retrofitting this device in a conventional hollow, intramedullary nail are disclosed herein. The bone fixation device of the invention generally comprises at least one blade member having a top portion registrable with a blade slot provided in the body of the nail, and a bottom surface including a rail slot, as well as at least one wedge member having an inclined top surface for transmitting a blade extending force to the bottom surface of the blade member, as well as a rail which is slidably engageable with the blade member slot. The blade slot and wedge rail interlock to provide a positive retracting force on the blade when it is desired to remove the nail from a bone. Additionally, the wedge member includes a key which interlocks with the longitudinal slot which extends along the longitudinal axis of a conventional Kuntscher intramedullary nail in order to facilitate angular alignment of the blade member with the blade receiving slot in the nail.

21 Claims, 7 Drawing Figures

U.S. Patent  May 27, 1986  Sheet 3 of 3  4,590,930
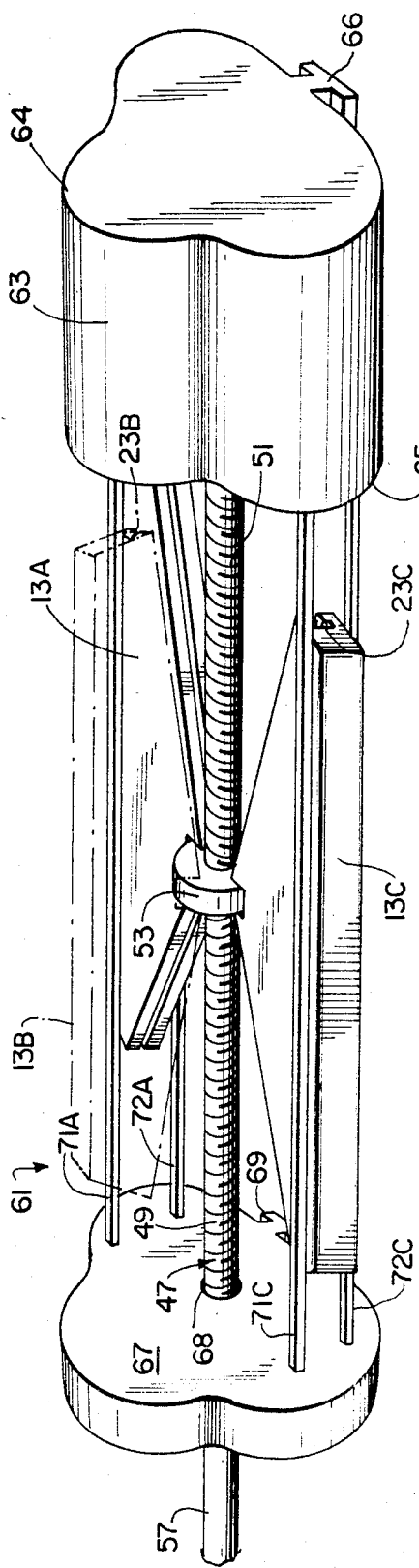
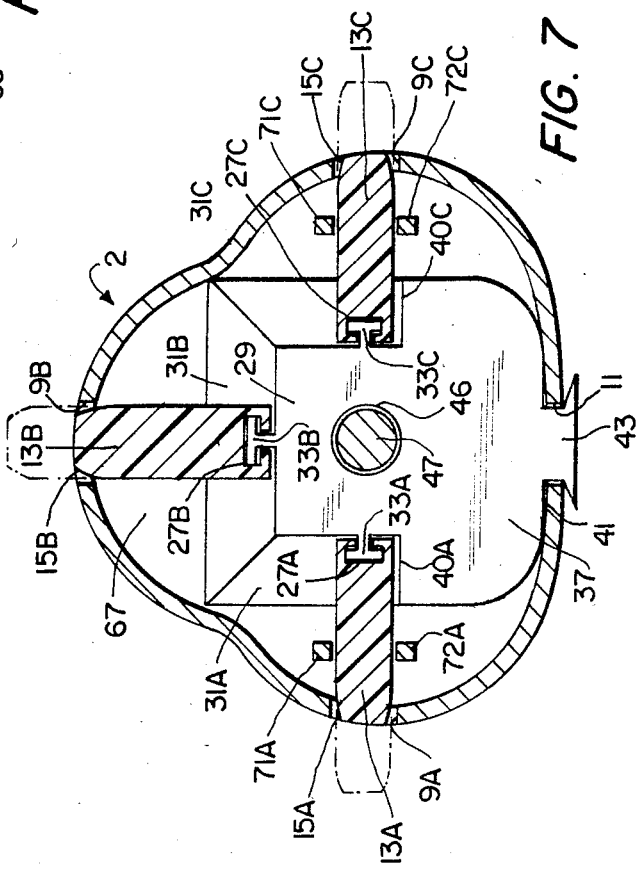

FIXATION DEVICE AND PROCESS FOR AN INTRAMEDULLARY NAIL

BACKGROUND OF THE INVENTION

1. Field of the Invention

This invention relates to a bone fixation device, and a process for retrofitting a fixation device in a hollow, intramedullary nail.

2. Discussion of the Prior Art

Intramedullary nails for treating fractures of long bones such as the femur, tibia, and humerus are well known in the prior art. One of the most popular intramedullary nails in use today was developed by Gerhard Kuntscher in the 1930's. This nail was extensively used by the Germans in World War II, and allowed them to quickly send many wounded Luftwaffe pilots with broken bones back into action without external braces. It is still used extensively today. Basically, the Kuntscher nail is a long, hollow stainless steel shaft having a cloverleaf cross-section, and a narrow slot running down its length. The back end of the nail terminates in an open mouth, while the front end of the nail terminates in a bullet-shaped nose to facilitate insertion into a fractured bone. In use, the intramedullary cavity of the bone is reamed out in accordance with standard orthopedic practice, and the bullet shaped nose of the nail is hammered into the medullary canal. After the nail is completely driven into the bone, the cloverleaf cross-section of the nail, coupled with the lateral resilience afforded by the longitudinal slot, effectively anchors the nail into the cortex of the proximal bone fragment, and in most instances also anchors the distal portion of the fracture against rotational movement. This feature is most important, since any rotational movement between the distal and proximal bone fragments during the healing process will non-align the reduction of the bone fracture and result in a malunited bone which may have to be corrected surgically.

While the Kuntscher cloverleaf nail is often capable of maintaining proper bone fragment alignment during the healing process, there are instances where it can fail. For example, if the fracture is located well into the distal portion of the bone where the intramedullary cavity rapidly flares out in cross-section, the distal end of the cloverleaf nail may fail to gain sufficient purchase on the flared surfaces of the bone cortex.

Heretofore, the prior art has attempted to solve this problem by designing special intramedullary nails having round cross-sections and which abandon the cloverleaf cross-section which renders the Kuntscher nail so effective and popular, and have switched over to a nail having a circular cross-section which relies almost entirely upon a distally located expanding mechanism to gain purchase in the cortex of the distal bone fragment. In one such design, the distal end of the nail is split into several sections along its longitudinal axis, and a conical member which rides on an axially disposed, threaded rod spreads the split ends of the nail apart when the rod is rotated. While this nail is capable of gaining purchase on the distal end of a bone fracture, this design is not without shortcomings. In addition to gaining poorer purchase on the proximal bone fragment as a result of the circular in lieu of the split cloverleaf cross-section, on or more of these split ends can break off when extended by the conical member. Furthermore, when it is necessary to remove the nail after the bone is healed, this design relies solely on the restorative resiliency of the split nail ends to retracted the expanded portion of the nail; a small piece of bone fragment lodged between the threaded rod and one or more of the split nail ends could frustrate the nail removal process. Additionally, because the lateral or transverse extension of the split nail ends is a nonlinear function of the degree of rotation of the threaded shaft, it is difficult for an orthopedic surgeon to determine with precision the degree to which the nail end has expanded by the number of wrench turns on the rod. Finally, because the longitudinal dimension of the nail contracts as a function of the nail end expansion, it is difficult for an orthopedic surgeon to tell, without numerous fluoroscopy readings, exactly where and how the nail is seated on the bone cortex.

Another approach to solve the anchoring problem associated with conventional Kuntscher cloverleaf nails has been to design a nail having a circular cross-section and blades or spikes which can extend out the sides of the distal portion of the nail. However, like the "split end" nails, the abandonment of the resilient cloverleaf cross-section in favor of a circular cross-section impairs the ability of the nail to gain purchase on the cortex of the proximal bone fragment. Additionally, the blades or spikes in some of these nails extend from their lateral ports or slots in a pivoting motion, as opposed to a straight lateral motion. Such pivoting actions are often controlled by cam mechanisms in which there is no simple linear relationship between the amount of transverse extension of the blades or spikes, and the number of turns on the threaded rod. Sucn nonlinearity, of course, makes it difficult for the orthopedic surgeon to easily determine the degree of expansion that the blades or spikes of the device have undergone as a result of the number of wrench turns he has applied to the threaded rod of the device. Moreover, while some of these mechanisms do not rely entirely upon the resiliency of the blade material to retract the blades, the retracting mechanisms employed are unduly complicated, rely on close tolerances in order to function effectively, and are not designed to be retrofitted in any conventional hollow, intramedullary nail.

Clearly, a need exits for a simple, effective expansion device having a set of laterally extendible blades which can be transversely expanded or retracted with precision as a simple function of the number of turns of an elongated control member, and which may easily be retrofitted onto a Kuntscher cloverleaf nail in order to retain the advantages associated with a split cloverleaf cross-section. Ideally, such an expansion device should be simple and inexpensive in construction, and should not rely upon close tolerances in its fabrication in order to afford near-perfect reliability in operation.

SUMMARY OF THE INVENTION

In its broadest terms, the invention is both a bone fixation apparatus, and a process for retrofitting this apparatus in a hollow, intramedullary nail.

The retrofittable fixation apparatus or device of the invention generally comprises at least one blade member having a top portion which is registrable with a slot provided in the body of the nail, and a bottom portion including a rail slot, at least one wedge member having a rail which is slidably engageable with the slot of the blade, and an elongated member for moving the wedge member into and away from the blade. The wedge member extends or retracts the blade member in direct proportion to the distance, the elongated member moves the wedge into or away from the blade member, thereby rendering it easy for the surgeon to control with precision the degree to which the blades are extended and retracted. The rail of the wedge member may interlock with the slot of the blade member so that any withdrawal forces applied to the wedge member are effectively transmitted as retracting forces on the blade member throughout the entire length of the rail engaging the slot of the blade member. Also, the bone fixation device may have two wedge members which move in opposite directions during the extending and the retracting process in order to neutralize longitudinal forces on the blade members, thereby preventing malignment of the blade members with their respective slots. Finally, either the blade member, or the wedge member may be formed from a biologically inert, resilient material in order that the blade members may "snap fit" into the slots provided in the nail when said device is retrofitted into a hollow, intramedullary nail.

In the process of the invention, a slot is provided in the body of an intramedullary nail which may be registered with each blade in the expansion device. This nail may be a conventional Kuntscher cloverleaf nail. A detent may next be punched into the body of the nail for stopping the movement of the expansion device at a selected point along the longitudinal axis of the body of the nail where the blade members will be in longitudinal alignment with their respective blade slots when the device is completely inserted into the nail. In the alternative, the device may be designed so that proper longitudinal blade alignment occurs when the device is snugged into the nose of the nail. Key members are then provided in at least one of the wedge members which may slidably engage the longiudinal slot present in Kuntscher type nails in order to maintain the blade members in proper angular alignment with their respective slots when the device is completely inserted into the nail. Next, the expansion device is inserted along the longitudinal axis of the body of the nail until stopped by the detent, or snugged into the nose of the nail. Finally, the blade members are extended and retracted as necessary.

As a further step in the process of the invention, the blade members may be extended slightly before the device is inserted into the nail so that the blade members "snap fit" with their respective slots when the device is inserted up to the detent or nose of the nail body.

BRIEF DESCRIPTION OF THE SEVERAL FIGURES

FIG. 6 is a side, perspective view of the alignment assembly of the preferred embodiment of the invention; and FIG. 7 is a cross-sectional view of the fixation device illustrated in FIG. 3, taken along the line 7—7.

DETAILED DESCRIPTION OF THE PREFERRED EMBODIMENT

Figure 1:
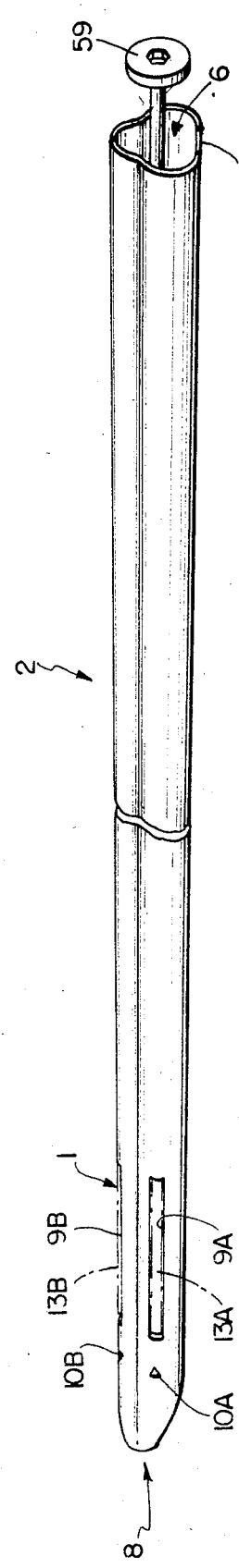
FIG. 1 is a perspective view of a Kuntscher-cloverleaf nail retrofitted with the fixation device of the invention.
Figure 2:
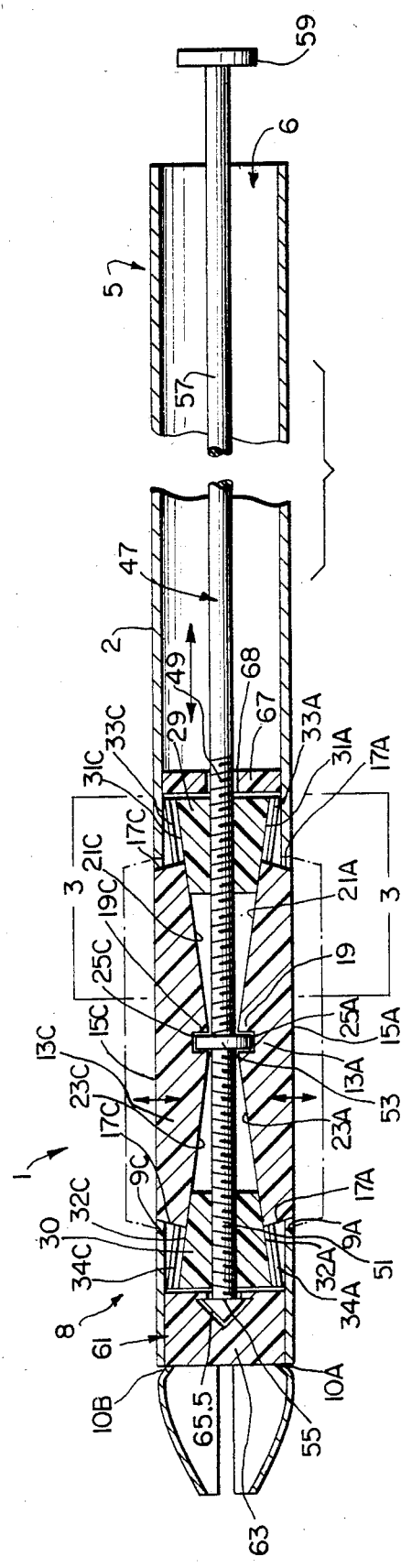
FIG. 2 is a plan view of the nail illustrated in FIG. 1, showing a cross-sectional view of a preferred embodiment of the fixation device of the invention.

With reference now to FIGS. 1 and 2, wherein like numerals designate like parts of the invention, the preferred embodiment of the invention is a fixation device 1 for a Kuntscher cloverleaf intramedullary nail 2. While the instant nail is straight, such nails may be slightly curved along their longitudinal axes in order to conform to the contour of human bones, such as the femur. Such nails have a proximal portion 5 which typically terminates in an open end 6, and a distal portion 8, which terminates in a bullet-shaped tip, as shown. In order that the fixation device 1 of the invention may be retrofitted into the nail 2, three, blade receiving slots 9A, 9B and 9C are cut or punched in the distal portion 8 of the nail 2 as shown. The distal portion 8 of the nail 2 also preferably includes three detents 10A, 10B and 10C for facilitating the longitudinal alignment of the blade members 13A, 13B and 13C with their perspective slots 9A, 9B and 9C when the device 1 is inserted into the open end 6 of the nail 2 and completely slidden into its operative position in the distal end 8. Finally, the nail 2 normally has a longitudinal slot 11 extending the entire length of its bottom, as is best seen in FIG. 1. It is important to note that the slot 11 is not cut or punched especially in the nail 2 so that the fixation device 1 may be easily retrofitted thereto; rather it is a normal structural feature of a conventional, Kuntscher cloverleaf nail which is deliberately placed in the nail 2 to afford a degree of lateral resilience which would not exist if slot 11 were not present. This lateral resilience helps the nail 2 to gain purchase in the central, narrow portion of the intramedullary canal of a bone.

As used herein, the term "retrofit" is used in its most general sense in that the Kuntscher cloverleaf nail 2 need not have actually been in service in a bone before being fitted with the fixation device 1 of the invention. The terms "retrofit" and "retrofittable into" are frequently used throughout the balance of the specification because they concisely underscore one of the primary advantages of the invention, i.e., the ability of the fixation device 1 to be easily used in connection with a conventional, commercially available intramedullary nail.

Figure 3:
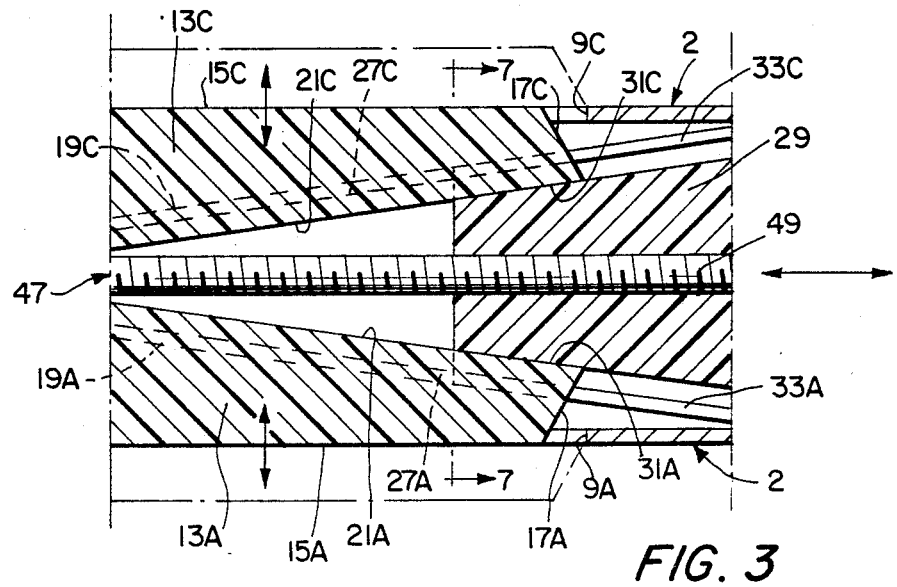
FIG. 3 is an enlargement of the cross-sectional view illustrated in FIG. 2, taken along the section designated 3—3 in FIG. 2.

Turning now to FIGS. 2 and 3, the fixation device 1 generally comprises three blade members 13A, 13B and 13C, a pair of opposing wedge members 29, 30, a threaded rod 47, and an alignment assembly 61.

Figure 5:
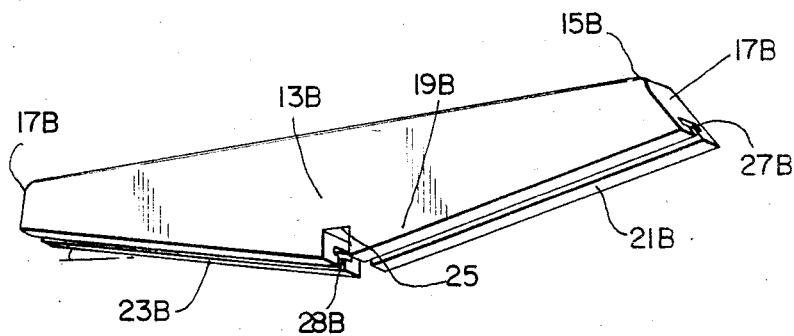
FIG. 5 is a side, perspective view of one of the blade members in the preferred embodiment of the fixation device of the invention.

Each of the blades 13A, 13B and 13C has a top portion 15A, 15B and 15C which terminates in a tapered or rounded top surface, as shown. Such tapering or rounding of the top surfaces of the blades 13A, 13B and 13C helps render them self-aligning with their respective blade slots 9A, 9B and 9C angular axis of the nail 2. Additionally, each of the blade members 13A, 13B and 13C includes a pair of tapered shoulders 17A, 17B and 17C to facilitate the alignment of the blade members with their respective blade slots along the longitudinal axis of the nail 2 when the wedge members 29, 30 move toward one another on the threaded rod 47 and apply an extending force on the blade members. The bottom portions 19A, 19B and 19C of each of the blade members 13A, 13B and 13C each include a pair of wedge engaging, inclined surfaces, as shown. Specifically, the bottom surfaces of the blade members 13A, 13B and 13C each include a right inclined surface 21A, 21B and 21C, respectively, and a left inclined surface 23A, 23B and 23C, respectively. These bottom, inclined surfaces 21A, 21B and 21C, and 23A, 23B and 23C, each flatly engage a parallel top surface on opposing wedge members 29 and 30 in a manner which will be set forth in detail hereinafter. Centrally disposed in each of the blade members 13A, 13B and 13C is a central notch 25A, 25B and 25C, respectively. These notches 25A, 25B and 25C receive an integrally formed disc 53 on threaded rod 47 when the blades are completely retracted, as shown in FIG. 2. Finally, (as is best seen in FIGS. 3 and 5), each of the bottom portions 19A, 19B and 19C of blade members 13A, 13B and 13C includes a T-shaped slot 27A, 28A, 27B, 28B, and 27C, 28C, on each of its wedge engaging, inclined surfaces, respectively.

Figure 4:
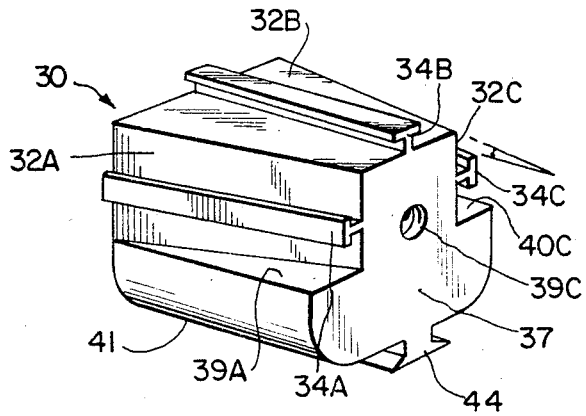
FIG. 4 is a side, perspective view of the left wedge member of the preferred fixation device illustrated in FIG. 2.

With reference now to FIGS. 2, 3 and 4, each of the opposing wedge members 29, 30 includes three inclined plane surfaces 31A, 31B, 31C and 32A, 32B and 32C which flatly engage the inclined bottom surfaces 21A, 21B and 21C and 23A, 23B and 23C of blade members 13A, 13B and 13C, respectively. As is indicated in FIG. 4, the inclined plane surfaces 31A, 31B and 31C and 32A, 32B and 32C of the wedge members 29, 30 are parallel to the inclined surfaces 21A, 21B and 21C, and 23A, 23B and 23C of the blade members 13A, 13B and 13C. This arrangement affords effective transfer of an extending force along a broad portion of the inclined surfaces 21A, 21B and 21C and 23A, 23B and 23C of the blade members 13A, 13B and 13C when the opposing wedge members 29, 30 are moved toward one another via threaded rod 47. This arrangement also results in a simple linear relationship between the amount of lateral extension of the blades 13A, 13B and 13C, and the number of turns on the threaded rod 47. Additionally, each of the wedge members 29, 30 includes three T-shaped rails 29A, 29B and 29C and 30A, 30B and 30C, respectively. As is best shown in FIG. 3, the rails 29A, 29B and 29C and 30A, 30B and 30C, are slidably engageable in the T-shaped slots 27A, 27B and 27C and 28A, 28B and 28C, of blade members 13A, 13B and 13C, respectively. The T-shaped rails serve two functions. First, the T-shaped rails maintain proper alignment between each of the blade members 13A, 13B and 13C and the inclined plane surfaces 29A, 29B and 29C and 30A, 30B and 30C of opposing wedge members 29, 30, respectively, when the inclined plane surfaces of the opposing wedges 29, 30 are moved toward the parallel inclined surfaces of the blade members 13A, 13B and 13C. More importantly, however, the T-shaped rails on the wedge members 29, 30 exert a positive, retracting force on the blade members 13A, 13B and 13C when the opposing wedge members 29, 30 are spread apart by threaded rod 47. Hence, the fixation device 1 of the invention does not rely upon the inherent resilience of any member to retract the blade or spike; rather, it utilizes an inclined, interlocking rail to positively retract its blade members 13A, 13B and 13C in direct proportion to the number of turns on threaded rod 47, as will be described in more detail hereinafter. As is best shown in FIG. 4, the bottom portion of wedge member 30 includes a rectangular block 37 having two blade member-engaging faces 39A, 39C. The blade member-engaging faces 39A, 39C help properly align blade members 13A, 13C onto the wedge member 30 by providing support on one side of each of these blade members. The rectangular block 37 of the wedge member 30 terminates in slightly rounded bottom surface 41 which conforms to the slightly rounded surface of the Kuntscher cloverleaf nail, as is best shown in FIG. 7. Finally, the bottom surface 41 of block 37 includes a key member 43 which can slidably interlock with the longitudinal slot 11 which runs normally along the longitudinal axis of the nail 2. Key member 43 anchors the blade members 13A, 13B and 13C of fixation device 1 in proper angular alignment with their respective slots 9A, 9B and 9C, and greatly facilitates the process of retrofitting the device 1 inside a standard, Kuntscher cloverleaf nail. Although the rectangular block 37, blade member-engaging faces 39A, 39C, block bottom surface 41, and interlocking key 43 have been described and illustrated in detail only with respect to wedge member 30, it will be understood that these same features are also present on wedge member 29, as wedge members 29 and 30 are preferably identical in construction.

In the preferred embodiment, although blade members 13A, 13B and 13C and wedge members 29, 30 may be made of surgical stainless steel, each is made of polyethylene, for three reasons. First, polyethylene is a proven biologically inert substance, and its presence in human bones does not damage bone tissues in any way. Secondly, polyethylene has a natural resilience which is useful in aligning the fixation device 1 with the blade receiving slots 9A, 9B and 9C of the nail 2; i.e., the blades can be extended slightly prior to insertion into the mouth 6 of the nail 2, which will cause them to "snap fit" when they are properly aligned with their respective slots. Finally, polyethylene is relatively inexpensive, and easy to mold and fabricate into the shapes of the blade 13A, 13B and 13C and wedge members 29, 30. Because polyethylene is transparent to X-rays, some sort of X-ray marker, such as a piece of stainless steel wire or foil (not shown), is preferably molded into each of the blade members 13A, 13B and 13C.

With reference now to FIGS. 2 and 6, the threaded rod 47 of the fixation device 1 includes a right hand thread 49, a left hand thread 51, and an integrally formed disc member 53 between the right and left hand threads 49, 51 as shown. Threaded rod 47 also includes a conical tip 55 on one end which may be "snap fitted" in to a recess 65.5 in distal stop 63, and a conventional Allen Head socket 59 on the other end which preferably includes a knurled rim so that the socket 59 may conveniently be finger-turned. The right hand thread 49 is threadably engaged to a centrally disposed threaded bore 47 in wedge member 29, while the left hand thread 51 is likewise threadably engaged in a threaded bore which is centrally disposed in wedge member 30. The integrally formed disc 53 disposed between the right hand thread 49 and left hand thread 51 is slidably received into central notches 25A, 25B and 25C located on the bottom surface of blade members 13A, 13B and 13C. Integrally formed disc 53 serves three important functions. First, the disc 53 preserves proper longitudinal alignment between each of the blade members 13A, 13B and 13C when the fixation device 1 is inserted into the mouth 6 of nail 2, and slided up into its proper position against detents 10A, 10B and 10C in the distal portion of the nail 2. This, in turn, affords additional insurance that the blade members 13A, 13B and 13C will properly register with their respective slots 9A, 9B and 9C when the device 1 is retrofitted into the nail 2 and expanded. Secondly, the disc 53 serves as a longitudinally oriented stop member when the opposing wedge members 29, 30 are completely moved toward one another incident to extending the blade members 13A, 13B and 13C. The stop-action that disc 53 exerts on the wedge members 29, 30 provides a clear, tactile signal to the orthopedic surgeon that blades 13A, 13B and 13C are completely extended, since the torque necessary to rotate rod 47 will increase dramatically when the opposing ends of wedges 29, 30 abutt opposite sides of disc 53. Thirdly, disc 53 functions as a laterally oriented stop member when the blades 13A, 13B and 13C are completely retracted, as the bottoms of the notches 25A, 25B and 25C will engage the edge of disc 53 in this position. Thus, disc 53 advantageously reinforces the function of the stops 63, 67, as will become more apparent hereinafter. Threaded rod 47 further includes a shank portion 57, which terminates in an Allen Head socket 59 which is preferably knurled to facilitate finger-turning, as heretofore pointed out. The shank 57 transmits torque exerted from a hand or an Allen Head torque wrench (not shown) inserted into Allen Head socket 59 to the right hand thread 49 and left hand thread 51. The entire threaded rod 47 is preferably made from a biologically inert metal, such as surgical stainless steel.

With reference now to FIGS. 6 and 7, the fixation device 2 of the invention also includes an alignment assembly 61 which generally includes a distal stop 63, a proximal stop 67, and alignment bars 71A, 72A and 71C, 72C. The general purpose of the alignment assembly 61 is to insure that the blades 13A, 13B and 13C are properly aligned with their respective slots 9A, 9B and 9C when the device 1 is inserted into the mouth 6 of nail 2, both along the angular and longitudinal axis of the nail 2. Distal stop 63 preferably has a cross-sectional shape which is complementary to the cloverleaf cross-section of nail 2. In the preferred embodiment, the leading edge 64 of distal stop 63 is square, so that this edge can easily and effectively engage detents 10A, 10B and 10C punched into the distal portion 8 of nail 2. In the alternative, detents 10A, 10B and 10C may be dispensed with and the front portion of distal stop 63 may be given a "bullet-shape" complementary to the nose of the nail 2. Such an arrangement would also allow proper registry of the blades 13A, 13B and 13C when the device is completely inserted in nail 2, and snuggged into the nose of the nail 2. The distal stop 63 should be proportioned so that the rear edge 65 functions to stop wedge member 30 when member 30 is withdrawn to a point where blade members 13A, 13B and 13C are completely withdrawn from their respective slots 9A, 9B and 9C, thereby giving the orthopedic surgeon a clear tactile signal that the blade members 13A, 13B and 13C are completely retracted. Of course, the longitudinal length of distal stop 63 should be chosen so that the distance between leading edge 64 and the tapered shoulders of blades 13A, 13B and 13C corresponds to the distance between the detents 10A, 10B and 10C and the distal edges of the blade slots 9A, 9B and 9C. As previously mentioned, distal stop 63 further includes a conical recess 65.5 for receiving the conical tip 55 of threaded rod 47 in "snap-fit" fashion. Such a "snap fit" should be slightly loose so that the conical tip 55 of the threaded rod 47 is freely journalled in the distal stop 63. Finally, like wedge members 29, 30, distal stop 63 includes a key member 66 which slidably engages longitudinal slot 11 running down the length of nail 2. Key member 66 co-acts with the cloverleaf cross-sectional shape of distal stop 63 to maintain proper angular alignment of all of the blade members 13A, 13B and 13C of the fixation device 2 when the device 2 is completely inserted down the mouth 6 of the nail 2.

The alignment assembly 61 also includes a proximal stop 67, as shown. Like distal stop 63, the cross-sectional profile of proximal stop 67 is complementary to the cloverleaf cross-sectional profile of the nail 2. Proximal stop 67 also includes a smooth bore 68 through which threaded rod 47 freely passes without any engagement of right hand thread 49. Finally, like distal stop 63, proximal stop 67 also includes a key member 69 which slidably engages longitudinal slot 11 of nail 2 when the fixation device 1 is completely inserted through mouth 6 into the position shown in the distal portion 8 of the nail 2. Again, the cloverleaf profile of proximal stop 67 co-acts with its respective key member 69 to maintain proper angular alignment of the blades 13A, 13B and 13C of the device 2.

Finally, the alignment assembly 61 includes four alignment bars 71A, 72A, 71C, and 72C. There are three important functions associated with these alignment bars. First, the alignment bars 71A, 72A, 71C and 72C serve to space the proximal stop 67 at the proper point along the longitudinal axis of the fixation device 1 to arrest wedge member 30 when it has moved far enough back on right hand thread 49 to completely retract blades 13A, 13B and 13C out of blade slots 9A, 9B and 9C. Hence, proximal stop 67 reinforces the function of distal stop 63 and disc member 53 in providing a clear, tactile signal to the orthopedic surgeon turning Allen Head socket 59 of threaded rod 47 that the blades 13A, 13B and 13C are completely retracted. Secondly, alignment bars 71A, 72A, 71C and 72C insure that the fixation device 1 will not buckle or warp during its insertion down the length of nail 2, thereby throwing the various parts of the device 1 out of proper alignment with one another. Finally, the alignment bars 71A, 72A, 71C and 72C help properly align blade members 13A, and 13C, respectively, with slots 9A and 9C as is best seen in FIG. 7. It should be noted that each of these functions enhances the overall reliability of the fixation device 1, which is important in an operating room atmosphere where speed and effectiveness may make the difference between life or death. While alignment bars 71A, 72A, 71C, 72C may be made from a variety of biologically inert materials, a non-resilient inert material, such as surgical stainless steel, is preferred since such a material will enhance the clarity of the tactile signal given to the orthopedic surgeon informing him that wedge members 29, 30 have been completely retracted against stops 63 and 67.

Now that the preferred embodiment has been described, the preferred process of the invention will be set forth in detail.

In the first step of the preferred process of the invention, blade receiving slots 9A, 9B and 9C and detents 10A, 10B and 10C are cut or punched into the distal end of a standard Kuntscher, clover-leaf nail 2. Next, after the fracture has been reduced in accordance with standard orthopedic procedure, the interior of the broken bone is reamed to an appropriate nail accommodating diameter. In the third step of the process, a decision is made whether or not to retrofit fixation device 1 into the nail 2 before the nail is driven into the medullary canal of the broken bone. In order to make this decision, standard fluoroscopic techniques are used to determine the exact location of the fracture. If the fracture is far enough into the distal end of the bone so that there is a good chance that a standard Kuntscher cloverleaf nail 2 will not gain adequate purchase on the distal portion of the fragment, the fixation device 1 is retrofitted into the nail 2 in the following manner:

(1) First, the fixation device 1 is held with one hand while the knurled rim of Allen Head socket 59 of threaded rod 47 is finger-turned counterclockwise until wedge members 29, 30 abutt their respective stop members 63, 67 and the blade members 13A, 13B and 13C are completely retracted.

(2) Next, Allen Head socket 59 is turned a couple of turns clockwise so that the blade members 13A, 13B and 13C extend up a millimeter or so from their completely retracted position.

(3) The device 1 is then inserted into the mouth 6 of a Kuntscher cloverleaf nail provided with slots 9A, 9B, 9C and detents 10A, 10B, and 10C as heretofore described. When inserting the fixation device 1 into the nail 2, key member 66 of distal stop 63 is first slidably engaged into the longitudinal slot 11 which runs the length of the nail 2. The key members on the wedge members 30, 29, and the proximal stop 67 are likewise slidably engaged on the slot 11.

(4) Finally, the fixation device 1 is then completely inserted through the hollow interior of the nail 2 until the distal stop 63 engages detents 10A, 10B and 10C, at which time the blade members 13A, 13B, and 13C should "snap-fit" into registry with their respective slots 9A, 9B and 9C due to the fact that they were raised slightly prior to insertion and are formed from resilient polyethylene. To facilitate the insertion of the fixation device 1 into the interior of the nail 2, a sterile lubricant is preferably applied onto all of the nail engaging surfaces.

The nail is then driven through both the proximal and distal portions of the bone fragments in conformance with standard orthopedic techniques. Next, the blade members 13A, 13B and 13C are expanded in the distal portion of the bone fragment in order to gain adequate purchase on the bone cortex by applying torque via a torque wrench (not shown) onto Allen Head socket 59 of threaded rod 47. If the surgeon does not wish to completely extend the blades 13A, 13B and 13C, he may control the degree of expansion simply by counting the number of turns made on Allen Head socket 59. On the other hand, if complete blade extension is desired, the surgeon merely turns Allen Head socket 59 until the wedge members 29, 30 will abutt opposing sides of disc 53 of threaded rod 47, thereby sharply arresting the motion of the wedge members 29, 30. This, in turn, will create a sharp increase in the amount of torque needed to turn Allen Head socket 59, which will provide a tactile signal to the orthopedic surgeon that the blades 13A, 13B and 13C are completely extended.

In keeping with standard orthopedic process, the bone is given an additional fluoroscopic examination under a fluoroscope while being twisted gently in order to determine whether or not the nail 2 has gained adequate purchase in both the proximal and distal bone fragments.

After the bone has healed, the orthopedic surgeon retracts the blades 13A, 13B and 13C by turning Allen Head socket 59 counterclockwise until the wedge members 29, 30 abutt their respective stop members 63, 67. As previously described, the T-shaped rails 33A, 33B and 33C and 34A, 34B and 34C each apply a positive, retracting force to their respective, interlocking slots 27A, 27B and 27C and 28A, 28B and 28C, thereby pulling the blade members 13A, 13B and 13C back through their respective blade slots 9A, 9B and 9C. When the blades are completely retracted, the amount of torque required to turn Allen Head socket 59 counterclockwise will sharply increase, thereby providing a tactile signal to the orthopedic surgeon that the blades are completely retracted. The nail is then removed in the usual manner.

It should be noted that the instant device may advantageously be retrofitted on a standard nail which has already been driven in place in the bone medullary canal. In such a case, after a standard fluoroscopic examination shows that adequate purchase was not gained, the surgeon may perform device inserting steps 1 through 4 as heretofore described, and then resume standard orthopedic procedure.

Although the present invention has been described with reference to a preferred embodiment, it should be understood that the invention is not limited to the details thereof. A number of possible substitutions and modifications have been suggested in the foregoing detailed description, and others will occur to those of ordinary skill in the art. All such substitutions and modifications are intended to fall within the scope of the invention as defined in the appended claims.

What is claimed is:

1. A bone fixation device installable within a hollow, intramedullary nail having an open end, comprising:
  (a) at least one blade member having a top portion registrable with a blade slot provided in the wall of the nail, and a bottom surface including a rail slot;
  (b) at least one wedge member having an inclined top surface for transmitting a blade-extending force to said bottom surface of said blade member, and a rail which is slidably engageable with said slot for maintaining alignment between said top wedge surface and said blade member, and
  (c) an elongated member for applying a blade-extending force to said wedge member.

2. The bone fixation device defined in claim 1 wherein said elongated member applies a retracting force to said wedge member, and said rail of said wedge member interlocks with said slot of said blade member to transmit said retracting force to said blade member.

3. The bone fixation device defined in claim 2 wherein said rail has a "T"-shaped cross-section.

4. The bone fixation device of claim 1 wherein said blade is formed from a resilient material to facilitate the installation of the device into a nail by snap-fitting into said slot when said device is inserted in the open end of said nail and said blade is oriented in registry with said slot.

5. The bone fixation device of claim 1 wherein said wedge is formed from a resilient material in order to facilitate the installation of said device in said nail by snap-fitting said blade into said slot when said device is inserted through the open end of said nail and said blade is oriented in registry with said slot.

6. The bone fixation device defined in claim 1 having two opposing wedge members, each of which includes a rail which is slidably engageable with said slot of said blade member, and each of which has an inclined surface engageable with the bottom surface of the blade member for exerting a blade-extending force on said blade member when said elongated member forces said wedge members to move toward one another, while neutralizing the resultant of the longitudinal force component applied to the blade member by each of the inclined surfaces of the wedge members.

7. The bone fixation device defined in claim 6 wherein said elongated member is a threaded rod, and each of said wedge members are threadably engaged to said rod.

8. The bone fixation device defined in claim 7 wherein said threaded rod has a right hand thread on one portion and a left hand thread on the other portion, and one of said wedges is engaged to said right hand thread while the other of said wedges engages the left hand thread.

9. The bone fixation device defined in claim 1 wherein said nail has a slot running down its longitudinal axis, and said wedge member has a key member for slidably engaging said slot and facilitating the alignment of said blade member with said blade slot when said device is inserted through the open end of said nail and into its interior.

10. The bone fixation device defined in claim 1 further including a stop member for facilitating the alignment of said blade member with said blade slot by arresting the device at the proper point along the longitudinal axis of said nail.

11. The bone fixation device defined in claim 1 further including a stop member for limiting the distance that the wedge member may be moved into the blade member.

12. The bone fixation device defined in claim 1 wherein the top portion of said blade member is tapered to facilitate registry of said blade member with said blade slot when said device is inserted into the open end of said nail and retrofitted.

13. The bone fixation device defined in claim 1 wherein said blade member has a pair of opposing shoulders which stand adjacent to the ends of said blade slot when said blade member is inserted through said slot, and wherein said shoulders are tapered to facilitate proper registry of said blade member with said slot when said bone fixation device is inserted into the open end of said nail and said wedge member transmits a blade-extending force to said blade member.

14. An improved intramedullary nail of the type having a hollow, tubular body, a fixation means for fixing the nail to the intramedullary canal of a bone, and an elongated member located in the interior of the tubular body of the nail for operation said fixation means, wherein the improvement comprises an extendible and retractable fixation means comprising:
  (a) at least one blade member having a top portion extendible through a blade slot in the body of the nail, and a bottom surface including a rail slot, and
  (b) a wedge member having an inclined plane surface which engages said blade member when said elongated member moves said wedge member into said bottom surface of said blade member, thereby extending said blade member, and a rail which slidably engages said rail slot of said blade member and maintains alignment between said blade member and wedge member,
  whereby the distance said blade member is extended by said wedge member is directly proportioned to the distance said elongated member moves said wedge member toward said bottom surface of said blade member.

15. A process for installing a bone fixation device into a hollow, intramedullary nail having an open end, and a longitudinal slot along substantially all of its longitudinal axis, including the steps of:
  (a) providing at least one blade slot in the wall of said nail which is separate from said longitudinal slot;
  (b) providing a fixation device having an extendible blade member registrable with said blade slot, and a key member engageable with said longitudinal slot of said nail, and
  (c) inserting said device into said nail with said key member engaged to said longitudinal slot in order to achieve angular alignment of said blade member and said blade receiving slot.

16. The installation process defined in claim 15 further including the steps of:
  (a) providing a detent on the nail body at a selected point along the longitudinal axis of the nail;
  (b) providing a stop member on said fixation device, and
  (c) abutting said stop member against said detent in order to achieve proper longitudinal alignment between said blade member and blade slot.

17. A bone fixation device which may be installed in the interior of a hollow nail having an open end, a longitudinal slot present along substantially its entire length, and a blade slot which is separate from said longitudinal slot, comprising:
  (a) at least one blade member having a top portion which is extendible through said blade slot, and a bottom surface;
  (b) a key member engageable with said longitudinal slot for facilitating angular alignment between said blade member and said blade slot when said device is inserted through the open end of said nail, and
  (c) at least one movable wedge member having an inclined top surface for transmitting a blade-extending force to said bottom surface of said blade member when moved.

18. The bone fixation device of claim 17, further including a stop member for facilitating longitudinal alignment between said blade member and said blade slot.

19. The bone fixation device of claim 18, wherein said nail includes a detent for arresting said stop member when said device is inserted through the open end of the nail.

20. The bone fixation device of claim 19, wherein said nail includes two opposing blade slots, each of which is separate from said longitudinal slot, and wherein said device includes two blade members registrable with said blade slots.

21. A bone fixation device installable within a hollow, intramedullary nail having an open end and at least one slot in the wall of the nail which is substantially parallel to the longitudinal axis of the nail, and at least one separate blade slot in said wall comprising:
  (a) at least one blade member having a top portion registrable with said blade slot, and a bottom surface including a rail slot;
  (b) at least one wedge member having an inclined top surface for transmitting a blade-extending force to said bottom surface of said blade member, and a rail which is slidably engageable with said longitudinal slot for maintaining alignment between said top wedge surface and said blade member, and
  (c) an elongated member operatively connected to said wedge member for moving the wedge member substantially along the longitudinal axis of the nail in order to generate and to transmit a blade-extending force to said bottom surface of said blade member.

* * * * *